US007799357B2

(12) United States Patent
Ho et al.

(10) Patent No.: US 7,799,357 B2
(45) Date of Patent: Sep. 21, 2010

(54) **IN VITRO RESVERATROL-RICH CALLUS TISSUES DERIVED FROM *VITIS THUNBERGII* SIEB. ET ZUCC AND METHOD FOR PRODUCING THE SAME**

(75) Inventors: Chin-Wen Ho, Taipei (TW); Hsien-Shen Kuo, Taipei (TW)

(73) Assignee: Tatung Company (TW)

( * ) Notice: Subject to any disclaimer, the term of this patent is extended or adjusted under 35 U.S.C. 154(b) by 133 days.

(21) Appl. No.: 11/822,117

(22) Filed: Jul. 2, 2007

(65) Prior Publication Data

US 2008/0160560 A1 Jul. 3, 2008

(51) Int. Cl.
*A61K 36/87* (2006.01)
(52) U.S. Cl. ...................................... 424/766
(58) Field of Classification Search ........................ None
See application file for complete search history.

(56) References Cited

OTHER PUBLICATIONS

Kellet et al. Stilbene Accumulation in Grapevine Tissues: Developmental and Environmental Effects. Acta Hort. 514 . 2000. pp. 275-286.*
Lu. Micropropagation of *Vitis thunbergii* Sieb. Et Zucc., A Medicinal Herb, Through High Frequencyshot Tip Culture. Scientia Horticulturae 107. 2005. pp. 64-69.*
Keller et al. Stilbene Accumulation in Grapevine Tissues; Developmental and Environmental Effects. Acta Hortic. 514 . 2000. pp. 275-286.*
Mei-Chun Lu, "Micropropagation of *Vitis thunbergii* Sieb. et Zucc., a medicinal herb, though high-frequency shoot tip culture", Scientia Horticulturae vol. 107, 2005, pp. 64-69.
T. Hirabayashi et al., "In vitro Differentiation of Shoots from Anther Callus in *Vitis*[1]", HortScience, vol. 11(5), 1976, pp. 511-512.
M. Mii et al., "High-frequency callus formation from protoplasts of *Vitis labruscana* Bailey and *Vitis thunbergii* Sieb. et Zucc. by embedding in gellan gum", Scientia Horticulturae vol. 46, 1991, pp. 253-260.
Meishiang Jang et al, "Cancer Chemopreventive Activity of Resveratrol, a Natural Product Derived from Grapes", Science, vol. 275, Jan. 10, 1997, pp. 218-220.
George J. Soleas et al., "Resveratrol: A Molecule Whose Time Has Come? And Gone?", Clinical Biochemistry, vol. 30, No. 2, Mar. 1997, pp. 91-113.
Cecil R. Pace-Asciak et al, "The red wine phenolics *trans*-resveratrol and quercetin block human platelet aggregation and eicosanoid synthesis: Implications for protection against coronary heart disease", Clinica Chimica Acta, vol. 235, 1995, pp. 207-219.
Alexandra Hüsken et al., "Resveratrol glucoside (Piceid) synthesis in seeds of transgenic oilseed rape (*Brassica napus* L.)", Theor Appl Genet vol. 111, 2005, pp. 1553-1562.
Sunil K. Manna et al., "Resveratrol Suppresses TNF-Induced Activation of Nuclear Transcription Factors NF-κB, Activator Protein-1, and Apoptosis: Potential Role of Reactive Oxygen Intermediates and Lipid Peroxidation [1])", The Journal of Immunology, vol. 164, 2000, pp. 6509-6519.

* cited by examiner

*Primary Examiner*—Patricia Leith
*Assistant Examiner*—Melenie McCormick
(74) *Attorney, Agent, or Firm*—Fei-Fei Chao; Andrews Kurth LLP

(57) ABSTRACT

The present invention provides an in vitro resveratrol-rich callus tissue of *Vitis thunbergii* Sieb. et Zucc. which is a callus tissue developed from a tissue culture system containing one or more plant growth regulators (PGRs) and cultured from a stem or a petiole tissue explant of a wild type of *V. thunbergii* or a cultivated plantlet of *V. thunbergii*. The cultivated plantlet is in turn derived from a shoot of the wild type of *V. thunbergii* cultivated in a plantlet culture system containing no PGRs. The in vitro resveratrol-rich callus tissue of *V. thunbergii* is characterized by its containing at least about 1,000 to 10,000 mg/kg of dried weight of resveratrol, predominantly in the form of trans-resveratrol and/or resveratrol-O-glucoside, and being ready for harvest or subculture in about 30 days.

17 Claims, 7 Drawing Sheets
(4 of 7 Drawing Sheet(s) Filed in Color)

*trans*-Resveratrol (I)   *cis*-Resveratrol (II)

*trans*-Resveratrol-3-*O*-glucoside (III)   *cis*-Resveratrol-3-*O*-glucoside (IV)

IN VITRO RESVERATROL-RICH CALLUS TISSUES DERIVED FROM *VITIS THUNBERGII* SIEB. ET ZUCC AND METHOD FOR PRODUCING THE SAME

RELATED APPLICATION

This patent application claims the priority of Taiwan Patent Application No. 96100175, filed on Jan. 3, 2007, which is herein incorporated by reference.

FIELD OF THE INVENTION

The present invention relates to an in vitro resveratrol-rich callus tissue of *Vitis thunbergii* Sieb. et Zucc. (*V. thunbergii*) which is a callus tissue (hereinafter "the in vitro resveratrol-rich callus tissue") developed from a tissue culture system containing one or more plant growth regulators (PGRs) and cultivated from a stem or a petiole tissue explant of a wild type of *V. thunbergii* or a cultivated plantlet of *V. thunbergii*. The cultivated plantlet is in turn derived from a shoot of the wild type of *V. thunbergii* cultivated in a plantlet culture system containing no PGRs. The in vitro resveratrol-rich callus tissue of *V. thunbergii* is characterized by its containing at least about 1,000 to 10,000 mg of total resveratrol, predominantly in trans-resveratrol and/or trans-resveratrol-O-glucoside forms, per Kg of dried weight of the tissue. The in vitro resveratrol-rich callus tissue of *V. thunbergii* is ready for harvest or subculture after about 30 days in culture. The present invention further provides a method for cultivating the in vitro resveratrol-rich callus tissue, a method for extracting the resveratrol from the in vitro resveratrol-rich callus tissue, and a method for determining the resveratrol amount in the in vitro resveratrol-rich callus tissue by HPLC.

BACKGROUND OF THE INVENTION

Figure 1:
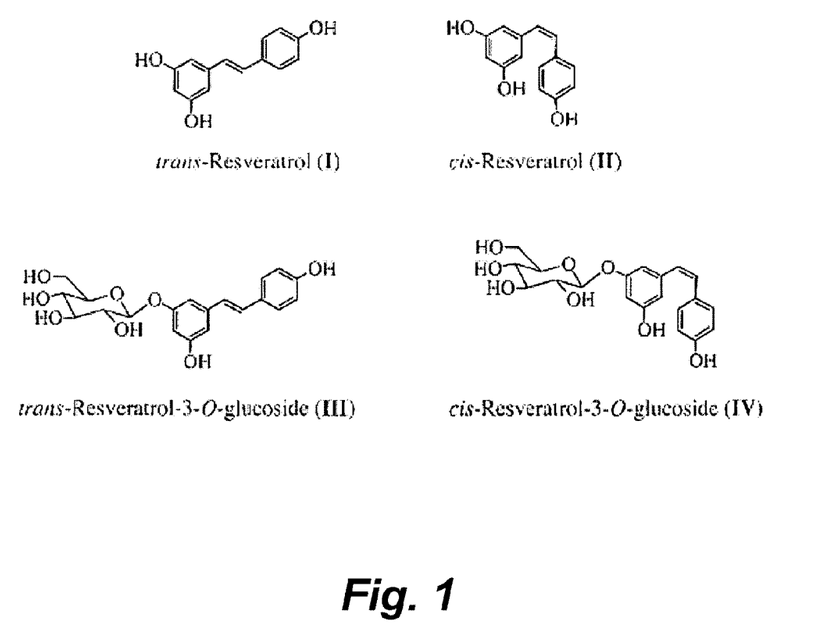
FIG. 1 shows the chemical structures of the major forms of resveratrol, which are cis- and trans-resveratrol and cis- and trans-resveratrol-O-glucoside.

Resveratrol (3,5,4'-trihydroxystilbene, RES) is a stilbene type compound found in varying amounts and structures (e.g., trans-, cis-, glucoside (piceid) etc.), as depicted in FIG. 1, infra. Resveratrol is produced by several plants, especially in grapes. It has also been produced by chemical synthesis.

Resveratrol is a phytoalexin (chemicals generated by a plant when it is subject to external stress) and has multiple biological activities. Resveratrol provides a number of beneficial effects, including anti-cancer, anti-inflammatory, antibacterial, antiviral, neuroprotective, anti-aging, and life-prolonging effects.

Resveratrol interferes with all three stages of carcinogenesis—initiation, promotion and progression. Experiments in cell cultures of varied types and isolated subcellular systems in vitro imply many mechanisms in the pharmacological activity of resveratrol. These mechanisms include modulation of the transcription factor NF-kB inhibition of the cytochrome P450 isoenzyme CYP1A1, alterations in androgenic actions and expression and activity of cyclooxygenase (COX) enzymes.

Resveratrol has been shown to induce apoptosis in some lineages of cancer cell culture (see, e.g., Sareen et al., *Investigative Ophthamology & Visual Science*, (2006), 47:3708-16) and reduce the probability of breast cancer occurrence (Subbaramaiah et al., *J. Biol. Chem.*, (1998), 273:21875-21882). The Chemoprevention Database reports six studies showing that small doses of dietary resveratrol can reduce colon carcinogenesis in rats and mice. Resveratrol is now under extensive investigation as a cancer chemopreventive agent.

Like many non-steroid anti-inflammatory drugs (NSAID), resveratrol has a chemically protective effect and can suppress COX-1, but will not induce action of COX-2 (cyclooxygenase-2) (see, e.g., Jang et al., *Science*, (1997), 275:218-220). It has also been reported that resveratrol DMSO solution could suppress the growth of bacteria *Staphylococcus aureus, Pseudomonas aeruginosa* and *Enterococcus faecalis*; as well as the growth of dermatophytes such as *Trichophyton mentagrophytes* and *Trichophyton rubrum* (Chan, *Biochem. Pharmacol.*, (2002), 63:99-104).

Moreover, resveratrol contained in red wines is very effective in preventing cardiovascular diseases and has extraordinary antioxidation characteristics and anticarcinogenicity. Frankel et al. (Frankel et al., *J. Agric Food Chem.*, (1995), 43:890-894) reported that trans-resveratrol can suppress the oxidation of low density lipoprotein (LDL) in human body. Studies showed that resveratrol prolongs the lifespan of the worm Caenorhabditis elegans and the fruit fly *Drosophila melanogaster* (Wood et al., *Nature,* (2004), 430:686-689). Resveratrol extended the maximum lifespan of a short-lived fish, *Nothobranchius furzeri*, by 59%, and extended its median lifespan by 56%. Also noted were an increase in swimming performance, an increase in cognitive performance, and a lack of neurofibrillary degeneration (Valenzano et al., *Current Biology*, (2006), 16:296-300). Recently, a report showed that resveratrol improves health and survival of mice on a high-calorie diet (Baur et al., *Nature*, 2006, 444: 337-342). In addition, resveratrol was reported effective against neuronal cell dysfunction and cell death, and in theory could help against diseases such as Huntington's disease (Parker et al., *Nature Genetics*, (2005), 4:349-50) and Alzheimer's disease (Marambaud et al., *J. Biol. Chem.*, (2005), 280:37377-82).

Efforts have been made to extract resveratrol from various plant sources and to promote production of resveratrol in plant cells by artificially providing stress. For example, Chung et al. (Chung et al., *Mol. Cells*, (2001), 12:353-9) reported that resveratrol contents in the leaves and roots of peanuts (*Arachis hypogaea* L. var. Jinpoong) were significantly increased when cultured in a medium containing yeast extract. Krisa et al. (Krisa et al., *J. Nat. Prod.*, (1999), 62:1699-1690) found that addition of jasmonic acid (JA) or its derivative methyl jasmonate (MeJA) increases the resveratrol content in cultured grape cells. It was also reported that UV radiation, sucrose concentration in the culture medium, and fungal infection may result in increased resveratrol content in grapes (see, e.g., Sarig et al., *Physiol. Mol. Plant Pathol.*, (1997), 50:337-347).

*Vitis thunbergii* Sieb. et Zucc. (*V. thunbergii*) is a plant in the grape category. The stem and twigs of *V. thunbergii* are a commonly used herbal medicine in Taiwan. It is believed to be effective in supplementing the kidneys, improving the eyesight, relieving rheumatic pains, removing toxins and supplementing the blood, and is mainly used to treat eye disease, rheumatism, rental deficiencies as well as lung disease, breast tumors, unknown swollenness, and hepatitis.

Many studies have been conducted on the cultivation of grape cells. Almost all the studies focused on the most common grape species of *Vitis vinifera*. There have been only a few studies related to tissue culture of *V. thunbergii*. For example, there was an attempt to use the anther of the *V. thunbergii* for plant regeneration, but only a small number of buds or calluses was reported to be generated from the studies. See Hirabayashi et al., *HortScience*, (1976), 11:511-512. There was another attempt by Mii et al., *Sci. Hortic.*, (1991), 46:253-260, which studied the formation of calluses from the protoplast of *V. labruscana* and *V. thunbergii* in a B5 modified medium. None of these studies, however, have focused on the studies of the resveratrol contents in the in vitro tissue.

SUMMARY OF THE INVENTION

The present invention provides an in vitro resveratrol-rich callus tissue derived from *Vitis thunbergii* Sieb. et Zucc. (*V. thunbergii*). The in vitro resveratrol-rich callus tissue is a callus tissue induced in a tissue culture system containing one or more plant growth regulators (PGRs) and cultured from a stem or a petriole tissue explant of a wild type of *V. thunbergii* or a cultivated plantlet of *V. thunbergii*. The in vitro resveratrol-rich callus tissue is characterized by its containing a total resveratrol amount which is at least about 1,000 to 10,000 mg/kg of dried weight (DW) of the tissue, preferably 3,000 to 8,000 mg/kg DW of tissue. The preferred in vitro resveratrol-rich callus tissue is cultured from the petiole explant of the wild type of *V. thunbergii* or the cultivated plantlet of *V. thunbergii*.

The cultivated plantlet is developed from the shoot of the wild-type *V. thunbergii* after growing in a plantlet culture system containing a carbohydrate and a Murashige and Skoog basic salt medium (MS medium) with no plant growth regulators (PGRs). The MS medium contains sodium, potassium, nitrate, ammonium, magnesium, sulfate, calcium, iron, chloride, phosphate, manganese, iodine, borate, zinc, copper, molybdenum, cobalt, or a mixture thereof. The preferred carbohydrate is myo-inositol or sucrose or a mixture thereof. A culture medium which contains an MS medium and a carbohydrate with no PGRs is called an "MS0 medium" in this invention. The cultivated plantlet is preferred to be grown in the MS0 medium for about 2 months to be ready for the stem or petiole tissue explant.

In addition to the PGRs, the tissue culture system used for callus induction further comprises an MS medium and a carbohydrate, which are similar to that of the plantlet culture system.

The preferred PGRs are α-naphthaleneacetic acid (NAA) and/or 6-benzyl-aminopurine (BA). Most favorably, the NAA is at a concentration of about 1.5 mg/L and BA is at a concentration of about 0.5 mg/L.

The tissue culture system further comprises a vitamin which is thiamine HCl, pyridoxine HCl, nicotinic acid, and mixtures thereof.

The preferred pH in the tissue culture system is about 5 to 7.

The most preferred tissue culture system for developing the in vitro resveratrol-rich callus tissue contains a carbohydrate, a half strength of Murashige and Skoog basic salt medium (i.e., ½ MS medium), about 1.5 mg/L of α-naphthaleneacetic acid (NAA) and about 0.5 mg/L 6-benzyl-aminopurine (BA).

The in vitro resveratrol-rich callus tissue is ready for harvest or subcultures after growing in the tissue culture system for about 30 days. The subcultures of the in vitro resveratrol-rich callus tissue is preferred to be carried out in a subculture medium containing a carbohydrate, a half strength MS medium (i.e., ½ MS medium), about 1.86 mg/L of α-naphthaleneacetic acid (NAA) and about 0.22 mg/L of 6-benzyl-aminopurine (BA) to maintain a good growth rate. The resveratrol amount in these subcultures of the in vitro resveratrol-rich callus tissue, however, reduced substantially, which are in the range of 500 to 4,000 mg/kg of dried weight (i.e., about 2,000-4,000 mg/kg of dried weight after the first subculture; about 1,000-2,000 mg/kg of dried weight after the second subculture; and about 500 to 1,000 mg/kg of dried weight after the third subculture).

The present invention further provides a method for obtaining the in vitro resveratrol-rich callus tissue from the stem or petiole tissue explant of the wild type of *V. thunbergii* or the cultivated plantlet of *V. thunbergii*. The method comprises the steps of: (1) inoculating the stem or the petiole tissue explant of the wild type *V. thunbergii* or the cultivated plantlet of *V. thunbergii* in the tissue culture system to induce the development of the callus tissue; and (2) growing the callus tissue in the tissue culture system for a sufficient amount of time to allow the callus tissue to be ready for harvest or subculture.

The tissue culture system contains one or more plant growth regulators (PGRs), such as α-naphthaleneacetic acid (NAA) and 6-benzyl-aminopurine (BA). The preferred concentration of NAA is about 1.5 mg/L and the preferred concentration of BA is about 0.5 mg/L. The tissue culture system is preferred to be sterilized, such as sterilized at about 121° C. under about 1.1-1.2 kg/cm² pressure for about 15 minutes. The tissue culture system is at about pH 5 to 7.

The cultivated plantlet is developed from a shoot of the wild type of *V. thunbergii* in a plantlet culture system, which comprises the MS0 medium as described above. The in vitro resveratrol-rich callus tissue is ready for harvest or subculture after being cultured in the tissue culture system for about 30 days.

The present invention further provides a method for extracting resveratrol from the in vitro resveratrol-rich callus tissue of *V. thunbergii*. The method comprises: (1) drying said in vitro resveratrol-rich callus tissue to obtain a dried resveratrol-rich callus tissue; (2) adding an alcohol to the dried resveratrol-rich callus tissue to form a suspension; (3) incubating the suspension for a sufficient amount of time; and (4) filtering the suspension after incubation to collect an filtrate which contains the extracted resveratrol. The preferred alcohol is methanol. The preferred suspension time is about 24 hours. The preferred filtration step is by passing the suspension through a 0.45 μm filter.

The preferred method for drying the resveratrol-rich callus tissue is by subjecting the resveratrol-rich callus tissue to freeze-drying. The resveratrol-rich callus tissue is frozen at about −80° C. for at least 10 hours and then transferred to a vacuum freeze-drying device for the freeze-drying.

Finally, the present invention provides a method for determining the extracted resveratrol amount in the in vitro resveratrol-rich callus tissue of *V. thunbergii* by injecting the extracted resveratrol filtrate to a high performance liquid chromatography (HPLC), and determining the extracted resveratrol amount at a wavelength of 307 nm using a resveratrol standard.

BRIEF DESCRIPTION OF DRAWINGS

The patent application file contains at least one drawing executed in color. Copies of this patent application publication with color drawing(s) will be provided by the office upon request and payment of the necessary fee.

FIG. 4 shows a high performance liquid chromatographic (HPLC) profile of the various forms of resveratrol extracted from the in vitro resveratrol-rich callus tissue developed from the petiole tissue explant of the cultivated plantlet of *V. thunbergii*. The plantlet was cultivated in an MS0 medium containing a MS medium and a carbohydrate without any plant growth regulators (PGRs) for about 2 months. The in vitro resveratrol-rich callus tissue was cultivated in a tissue culture system containing a carbohydrate, a half strength Murashige and Skoog basic salt medium (i.e., ½ MS medium), an about 1.5 mg/L of α-naphthaleneacetic acid (NAA) and an about 0.5 mg/L 6-benzyl-aminopurine (BA) for about 1 month. Both resveratrol and piceid were found in the tissue, as shown in the elution profile at about 6 minutes (i.e., piceid) and about 17 minutes (i.e., resveratrol).

FIG. 7 is a composite of pictures showing calluses derived from the stem explant of plantlet of *V. thunbergii* cultured for about one month on a modified MS medium with various NAA and BA concentrations for about one month. As shown in N1-1 to N1-5, when the tissue culture medium did not contain NAA, no callus was generated. When the tissue culture medium contained NAA in the concentration range of 0.5-1 mg/L and no BA (i.e., N2-1, and N3-1), the stem segments developed roots instead of calluses. The callus tissues were developed at the NAA concentration of 1.5 mg/L (i.e., N4-1 to N4-5). But without BA, only a small number of callus tissues was developed. The callus tissues, however, were developed nicely when the medium contained the BA concentration in the range of 0.5 to 2 mg/L. Most explants could only expand slightly without generating calluses. The best callus tissues were developed in the tissue culture system containing 1.5 mg/L of NAA and 0.5 mg/L of BA (i.e., N4-2). Bars represented 1 cm.

FIG. 8 is a composite of pictures showing calluses derived from the petiole explant of plantlet of *V. thunbergii* cultured for about one month in a modified MS medium with various amounts of NAA and BA. As shown in N1-1 to N1-5, when the tissue culture medium did not contain NAA, no callus was generated. When the tissue culture medium contained NAA in the concentration range of 0.5-1.5 mg/L and no BA (i.e., N2-1, N3-1, and N4-1), the petiole explants either developed no callus tissue (e.g., N4-1), or developed roots instead of calluses (e.g., N2-1 and N3-1). Contrary to the stem explant where only roots were developed in the N2-2 medium (See FIG. 7, N2-2), the petiole tissues developed loose calluses in the same medium. The petiole tissues also developed loose calluses in the N3-4 medium, while the stem tissues generated tumor shaped calluses in the same medium (See FIG. 7, N3-4). The best callus tissues from the petiole explants, however, were developed in the tissue culture system containing 1.5 mg/L of NAA and 0.5 mg/L of BA (i.e., N4-2). Bars represented 1 cm.

DETAILED DESCRIPTION OF THE INVENTION

Resveratrol is found in widely varying amounts in grapes (primarily the skins), raspberries, mulberries, in peanuts, berries of *Vaccinium* species, including blueberries, bilberries, and cranberries, some pines, such as Scots pine and eastern white pine, and the roots and stalks of giant knotweed and Japanese knotweed, called hu zhang in China.

The amount of resveratrol in food varies greatly. In grapes, resveratrol is found primarily in the skin and seeds. Fresh grape skin contains about 50 to 100 micrograms of resveratrol per gram of fresh weight. This is particularly true for muscadine grapes, whose skin and seeds have about 100 times the concentration as the pulp. The amount found in grape skins also varies with the grape cultivar, its geographic origin, and exposure to fungal infection. The amount of fermentation time a wine spends in contact with grape skins is an important determinant of its resveratrol content. Ordinary non-muscadine Red wine contains between 0.2 and 5.8 mg/L, depending on the grape variety, whilst white wine has much less, the reason being that red wine is fermented with the skins, allowing the wine to absorb the resveratrol, whereas white wine is fermented after the skin has been removed. Wines produced from muscadine grapes, however, both red and white, may contain more than 40 mg/L of resveratrol.

Peanuts have more than half the amount of resveratrol in red wine. The average amount of resveratrol in one ounce of peanuts in the marketplace (about 15 whole) is 79.4 μg/ounce. In comparison, some red wines contains approximately 160 μg/fluid ounce. The concentrations of resveratrol are similar in cranberry and grape juice. Blueberries have about twice as much resveratrol as bilberries, but there is great regional variation. These fruits have less than ten percent of the resveratrol of grapes. Cooking or heat processing of these berries will contribute to the degradation of resveratrol, reducing it by up to half.

Resveratrol (3,5,4'-trihydroxystilbene) is a polyphenolic phytoalexin having the following chemical structure:

Resveratrol is a stilbenoid, a derivate of stilbene. The biosynthetic pathway of resveratrol in plants involves stilbene synthase. Resveratrol is formed when stilbene synthase converts one molecule of p-coumaroyl-CoA and three molecules of malonyl-CoA into resveratrol, i.e., 3,5,4'-trihydroxystilbene. In some plant species, resveratrol production is inducible, and resveratrol accumulates as a phytoalexin following microbial attack. However, accumulation of resveratrol has been reported to have some negative side effects in plants. For example, Fischer, et al. reported that plants accumulating increased levels of resveratrol were rendered male sterile. Not only was the pollen destroyed, but the plants also demonstrated lower seed yields and altered flower color (Fischer, et al., *Plant J.* (1997), 11:489-498). Therefore, finding an in vitro tissue culture system to carry out the production of resveratrol clearly has economic values over a direct harvest of resveratrol from naturally existed plants.

Resveratrol exists as two structural isomers: cis-(Z) and trans-(E). Trans-resveratrol can undergo isomerization to the cis- form when heated or exposed to ultraviolet irradiation.

There are four major forms of resveratrol, which are cis and trans resveratrol, and cis and trans piceid (which is resveratrol-3-O-glucoside) (FIG. 1). These four forms of resveratrol are similar and related, and sometimes analyzed together as a group. Recent research demonstrated that trans-resveratrol possesses anti-cancer, anti-inflammatory, anti-bacterial, anti-viral, neuroprotective, anti-aging, and life-prolonging activities.

Piceid, also known as resveratrol-3-O-β-D-glucopyranoside (3,4',5-trihydroxystilbene-3-β-D-glucoside, or polydatin), or "resveratrol glucoside" ("RGluc") is a resveratrol conjugate. Both trans- and cis-RGluc have been isolated from nontransgenic plants, for example, grapes (Jeandet, et al., *Vitis*, (1994), 33:183-184), and *Eucalyptus sideroxylon* wood (Hillis, et al., *Phytochemistry* (1974), 13:1591-1595). It has been reported that human benefits previously thought to be due to resveratrol are also attributable to RGluc. Both cis- and trans-RGluc were listed among the active agents for providing valuable protection against cardiovascular disease.

The present invention provides an in vitro resveratrol-rich callus tissue which is characterized by the elevated content of resveratrol in the tissue, preferably containing at 1,000-10,000 mg/Kg dried weight (DW), and most favorably containing 3,000 to 8,000 mg/Kg DW, of the resveratrol amount (i.e., including both the resveratrol and piceid).

The in vitro resveratrol-rich callus tissue is a callus tissue derived from the stem or petiole tissue explant of *V. thunbergii*. A callus tissue contains a mass of somatic undifferentiated cells from an adult subject plant, which can be made to differentiate into the specialized tissues of a whole plant or a particular part of a plant, such as an adventitious root, with the addition of a number of hormones or enzymes.

The in vitro resveratrol-rich callus tissue can be obtained from culturing the stem or petiole tissue of the wild-type *V. thunbergii* in a tissue culture system containing at least one or more plant growth regulators, preferably α-naphthaleneacetic acid (NAA) and/or 6-benzyl-aminopurine (BA), and most favorably 1.5 mg/L of NAA and 0.5 mg/L of BA, for about a month. Alternatively, the in vitro resveratrol-rich callus tissue can be obtained from culturing the stem or petiole tissue of a cultivated in vitro plantlet, which in turn is developed from node culture of a wild type *V. thunbergii*. The node of the wild type *V. thunbergii* is cultivated in vitro into a plantlet, i.e., a young or small plant, in a plantlet culture system which comprises a Murashige and Skoog basic salt medium (i.e., MS medium or MS salts) without any plant growth regulator (i.e., MS0 medium) for about 2 months. The plantlet culture system is preferred to be a solid culture system.

The MS medium or MS salts referred to the salt composition described in Murashige & Skoog, *Physiol. Plant.*, (1962), 15, 473-497 (1962). It contains, without limitation, salt concentrations of ammonium nitrate, boric acid, calcium chloride, cobalt chloride, cupric sulfate, $Na_2$-EDTA, ferrous sulfate, magnesium sulfate, manganese sulfate, molybdic acid, potassium iodide, potassium nitrate, potassium phosphate monobasic, sodium nitrate, sodium phosphate monobasic and zinc sulfate. The standard MS salt composition is listed in Table 1. In certain embodiments, MS salts are used at half of the standard concentrations, which is referred to as "½ MS salts". As used herein, the term "MS salts" and "½ MS salts" are interchangeable with the term "MS media" and "½ MS media," respectively.

The tissue culture system for the callus formation, i.e., the in vitro resveratrol-rich callus tissue, is a solid or liquid culture system. The preferred system is the solid culture system. The tissue culture system contains a culture medium, which primarily contains one or more plant growth regulators (PGRs), such as indole-3-acetic acid (IAA), 2-4-dichlorophenoxyacetic acid (2,4-D), α-naphthaleneacetic acid (NAA), 6-benzyl-aminopurine (BA), kinetin, or a mixture thereof. The preferred PGRs for the callus formation is a combined use of NAA and BA, preferably at 1.5 mg/L of NAA and 0.5 mg/L of BA.

The culture medium also contains an MS medium and a carbohydrate. The preferred MS medium is at ½ MS salts. The preferred carbohydrate is myo-inositol or sucrose or a mixture thereof.

The culture media are adjusted to a pH range suitable for *V. thunbergii* growth. The pH range is preferably between 4 and 8, more preferably between 5 and 7, and most preferably around 5.7. The culture media may include suitable buffering agents for maintained the pH at the desired level. These agents will typically have a pKa between about 4.5 and about 5.5, and include, but are not limited to, citric acid, N-morpholino-ethansulfonic acid, potassium hydrogen phthalate, and benzoic acid.

Additionally, the culture medium can further optionally contain a vitamin, such as thiamine HCl, pyridoxine HCl, nicotinic acid, or a mixture thereof.

Furthermore, the temperature of the tissue culture is usually maintained at about 20-30° C., preferably at about 23-27° C., with a light cycle of 16 hours light illumination followed by 8 hours darkness. The light is preferably provided by cold white fluorescent light tubes at about 20-24 $\mu mol\ m^{-2}\ sec^{-1}$.

The present invention also provides a method for determining resveratrol content in *V. thunbergii* tissues. The method includes the steps of drying the tissues of interest, grinding the dried tissues, extracting the ground tissues with an alcohol to produce an extractant, and detecting the amount of resveratrol in the extractant by high performance liquid chromatography (HPLC), preferably using a uses a TOSOH TSK-gel ODS-80™ column.

The tissues may be dried with any method, preferably by freeze-drying using a refrigerated vacuum drier. The alcohol may be any alcohol, preferably methanol, ethanol, or isopropanol, and most favorably methanol. The extracting step is preferably performed by mixing the ground tissues with the alcohol to form a mixture, incubating the mixture at room temperature (i.e., 25 2° C.) for a sufficient amount of time, preferably for 24 hours, and filtering the incubated mixture to obtain the extractant.

The following experimental designs and result are illustrative, but not limiting the scope of the present invention. Reasonable variations, such as those occur to reasonable artisan, can be made herein without departing from the scope of the present invention. Also, in describing the invention, specific terminology is employed for the sake of clarity. However, the invention is not intended to be limited to the specific terminology so selected. It is to be understood that each specific element includes all technical equivalents which operate in a similar manner to accomplish a similar purpose.

EXAMPLES

Example 1

Material and Methods

Plant Materials

*Vitis thunbergii* Sieb. et Zucc. plants were obtained from the Tao Yuan Agricultural Improvement Farm. Plant tissues were sterilized and placed into various culture media. The shoots of the *V. thunbergii* plants were induced and developed.

Figure 2:
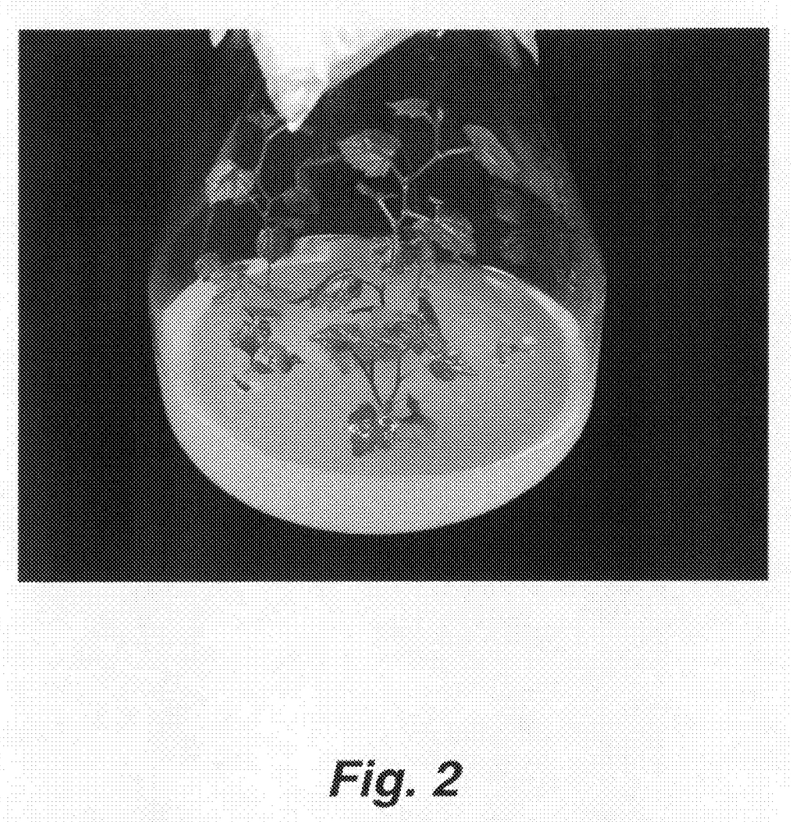
FIG. 2 shows a cultivated plantlet from a wild type of *Vitis thunbergii* Sieb. et Zucc. incubated on an MS0 medium for about two months.

The shoots were cultivated in a solid medium which contained MS salts and a carbohydrate (such as myo-inositol or sucrose or a mixture thereof) with no PGRs (i.e., a MS0 medium). In about 2 months, a complete plantlet was produced from each shoot, as shown in FIG. 2. The plantlet was sub-divided into leaf, stem, and petiole three different tissue explants for induction of the in vitro resveratrol-rich callus tissue.

Culture Medium

Various plant growth regulators (PGRs) and other cultural factors were added to the tissue culture medium containing MS salts as shown in Table 1. Unless otherwise noted, all media were supplemented with 30 g/L sucrose, 10 mg/L thiamine-HCl, 1 mg/L pyridoxine-HCl, 1 mg/L nicotinic acid, and 100 mg/L myo-inositol. As used hereinafter, the "MS0 medium" refers to a basic culture medium which contains MS salts, 30 g/L sucrose, 10 mg/L thiamine-HCl, 1 mg/L pyridoxine-HCl, 1 mg/L nicotinic acid, and 100 mg/L myo-inositol, has a pH value of 5.7, and does not contain any PGRs. The "½ MS medium" refers to a basic culture medium that contains ½ MS salts, 30 g/L sucrose, 10 mg/L thiamine-HCl, 1 mg/L pyridoxine-HCl, 1 mg/L nicotinic acid, and 100 mg/L myo-inositol, has a pH value of 5.7, and does not contain any PGRs.

The solid culture medium was prepared by adding 8 g/L agar to the liquid culture medium. Culture in solid medium was conducted in culture tubes of 8×3×3 cm³ or 15×2×2 cm³ size containing 10 ml culture medium, or in wide mouth bottles containing 25 ml culture medium. The openings of all culture containers were covered with aluminum foil. All of the culture media had a pH value of 5.70 0.05, and were sterilized by autoclaving at 121° C., under 1.1-1.2 kg/cm² pressure, for 15 minutes.

TABLE 1

The MS Basal Salts Composition (Murashige and Skoog, 1962)

| Chemical | mg/L |
|---|---|
| Macronutrients | |
| $KNO_3$ | 1900 |
| $NH_4NO_3$ | 1650 |
| $MgSO_4 \cdot 7H_2O$ | 370 |
| $CaCl_2 \cdot 2H_2O$ | 440 |
| $KH_2PO_4$ | 170 |
| Micronutrients | |
| $MnSO_4 \cdot 4H_2O$ | 22.3 |
| KI | 0.83 |
| $H_3BO_3$ | 0.2 |
| $ZnSO_4 \cdot 7H_2O$ | 8.6 |
| $CuSO_4 \cdot 5H_2O$ | 0.025 |
| $Na_2MoO_4 \cdot 2H_2O$ | 0.25 |
| $CoCl_2 \cdot 6H_2O$ | 0.025 |
| $FeSO_4 \cdot 7H_2O$ | 27.8 |
| $Na_2EDTA$ | 37.3 |

Tissue Culture Conditions

Unless otherwise noted, all tissue culture was performed at 25±2° C. Cold fluorescent light tubes (20-24 µmol m$^{-2}$ sec$^{-1}$) were used to provide light illumination, with a illumination cycle of 16 hours of light and 8 hours of darkness.

In Vitro Resveratrol-Rich Callus Tissue Induced by Different Explants

Tissues obtained from three different portions of the cultivated in vitro plantlet (stems (S), leaves (L) and petioles (P)) were placed into the tissue culture media containing MS salts and different concentrations of NAA (0, 0.5, 1, 1.5 and 2 mg/L) and BA (0, 0.5, 1, 1.5 and 2 mg/L) (Table 2). The callus tissues were examined about one month later. The experiment was repeated five times.

TABLE 2

Composition of ½ MS Media Modified for Callus Induction from Stem, Leaf and Petiole Explants of *Vitis thunbergi* Sieb. et Zucc.

| Composition(mg/L) | Media | | | | | | | | | |
|---|---|---|---|---|---|---|---|---|---|---|
| | N1-1 | N1-2 | N1-3 | N1-4 | N1-5 | N2-1 | N2-2 | N2-3 | N2-4 | N2-5 |
| | 1. | | | | | | | | | |
| Mineral composition | ½ MS | ½ MS | ½ MS | ½ MS | ½ MS | ½ MS | ½ MS | ½ MS | ½ MS | ½ MS |
| Organic substance | | | | | | | | | | |
| Thiamine-HCl | 10 | 10 | 10 | 10 | 10 | 10 | 10 | 10 | 10 | 10 |
| Pyridoxine-HCl | 1 | 1 | 1 | 1 | 1 | 1 | 1 | 1 | 1 | 1 |
| Nicotinic acid | 1 | 1 | 1 | 1 | 1 | 1 | 1 | 1 | 1 | 1 |
| Myo-inositol | 100 | 100 | 100 | 100 | 100 | 100 | 100 | 100 | 100 | 100 |
| Plant growth regulator | | | | | | | | | | |
| NAA | 0 | 0 | 0 | 0 | 0 | 0.5 | 0.5 | 0.5 | 0.5 | 0.5 |

TABLE 2-continued

Composition of ½ MS Media Modified for Callus Induction from Stem, Leaf and Petiole Explants of *Vitis thunbergi* Sieb. et Zucc.

| | | | | | | | | | | |
|---|---|---|---|---|---|---|---|---|---|---|
| BA | 0 | 0.5 | 1 | 1.5 | 2 | 0 | 0.5 | 1 | 1.5 | 2 |
| Sucrose (g/l) | 30 | 30 | 30 | 30 | 30 | 30 | 30 | 30 | 30 | 30 |
| pH | 5.7 | 5.7 | 5.7 | 5.7 | 5.7 | 5.7 | 5.7 | 5.7 | 5.7 | 5.7 |

| | Media | | | | | | | | | |
|---|---|---|---|---|---|---|---|---|---|---|
| Composition(mg/L) | N3-1 | N3-2 | N3-3 | N3-4 | N3-5 | N4-1 | N4-2 | N4-3 | N4-4 | N4-5 |
| 2. | | | | | | | | | | |
| Mineral composition | ½ MS | ½ MS | ½ MS | ½ MS | ½ MS | ½ MS | ½ MS | ½ MS | ½ MS | ½ MS |
| Organic substance | | | | | | | | | | |
| Thiamine-HCl | 10 | 10 | 10 | 10 | 10 | 10 | 10 | 10 | 10 | 10 |
| Pyridoxine-HCl | 1 | 1 | 1 | 1 | 1 | 1 | 1 | 1 | 1 | 1 |
| Nicotinic acid | 1 | 1 | 1 | 1 | 1 | 1 | 1 | 1 | 1 | 1 |
| Myo-inositol | 100 | 100 | 100 | 100 | 100 | 100 | 100 | 100 | 100 | 100 |
| Plant growth regulator | | | | | | | | | | |
| NAA | 1 | 1 | 1 | 1 | 1 | 1.5 | 1.5 | 1.5 | 1.5 | 1.5 |
| BA | 0 | 0.5 | 1 | 1.5 | 2 | 0 | 0.5 | 1 | 1.5 | 2 |
| Sucrose (g/l) | 30 | 30 | 30 | 30 | 30 | 30 | 30 | 30 | 30 | 30 |
| pH | 5.7 | 5.7 | 5.7 | 5.7 | 5.7 | 5.7 | 5.7 | 5.7 | 5.7 | 5.7 |

| | Media | | | | |
|---|---|---|---|---|---|
| Composition(mg/L) | N5-1 | N5-2 | N5-3 | N5-4 | N5-5 |
| Mineral composition | ½ MS | ½ MS | ½ MS | ½ MS | ½ MS |
| Organic substance | | | | | |
| Thiamine-HCl | 10 | 10 | 10 | 10 | 10 |
| Pyridoxine-HCl | 1 | 1 | 1 | 1 | 1 |
| Nicotinic acid | 1 | 1 | 1 | 1 | 1 |
| Myo-inositol | 100 | 100 | 100 | 100 | 100 |
| Plant growth regulator | | | | | |
| NAA | 2 | 2 | 2 | 2 | 2 |
| BA | 0 | 0.5 | 1 | 1.5 | 2 |
| Sucrose (g/L) | 30 | 30 | 30 | 30 | 30 |
| pH | 5.7 | 5.7 | 5.7 | 5.7 | 5.7 |

Subcultures of In Vitro Resveratrol-Rich Callus Tissue and Analysis of Resveratrol Content The in vitro resveratrol-rich callus tissue could be harvested or subcultured after being cultivated in the tissue culture system for about a month. In the first passage of the callus subculture, about 1 g (fresh weight) of the in vitro resveratrol-rich callus tissue was inoculated into a fresh solid subculture medium containing ½ MS medium with 1.86 mg/L of NAA and 0.22 mg/L of BA, and cultured for about 1 month. In the second passage of the subculture, about 1 g (fresh weight) of the first callus subculture was inoculated into a fresh solid subculture medium containing ½ MS medium with 1.86 mg/L of NAA and 0.22 mg/L of BA, and cultured for about another 1 month. In the third passage of the subculture, about 1 g (fresh weight) of the second callus subculture was inoculated into a fresh solid subculture medium containing ½ MS medium with 1.86 mg/L of NAA and 0.22 mg/L of BA, and cultured for yet about another 1 month.

Analysis of Resveratrol Content in Wild Type (Field Grown) *V. thunbergii* Plant Dried plants of *Vitis thunbergii* Sieb. et Zucc. were purchased from Gee-An Village, Hwa-Lian Hsien. The plants were ground into powders for resveratrol extraction and determination of resveratrol content.

Resveratrol Extraction

The tissue was weighted and frozen in a −80° C. refrigerator for 10 hours or longer. The frozen tissue was dried in a frozen vacuum drier (VirTis Freezemobile 12XL). The completely dried tissue was weighted to determine the dry weight and ground into fine powders. About 0.1 g of the powders were placed into a centrifugal tube and extracted with 5 ml methanol for 24 hours (25 2° C.). The mixture was then filtered through a 0.45 μm filter, and the extractant was placed into a 1.5 ml brown eppendorf and kept in a −5° C. refrigerator until HPLC analysis.

Resveratrol Standard

The trans-resveratrol standard was purchased from Sigma (St. Louis, USA). The piceid standard was purchased from Chromadex INC.(St. Santa Ana, Calif.).

HPLC Analysis of Resveratrol

A JASCO PU-1580 intelligent HPLC pump and a JASCO UV-1570 intelligent UV/VIS detector were used for the HPLC analysis. Measurement conditions were according to Burns et al. (Burns J. et al., *J. Agric. Food Chem.*, (2002), 50:3337-3340) with modification. The pipe column was TOSOH TSK-gel ODS-80 TM (4.6×250 mm), and the mobile phase was acetonitrile: $H_2O=25:75$(v/v), with a flow velocity of 1 ml/min. Resveratrol was detected at 307 nm wavelength.

Figure 3:
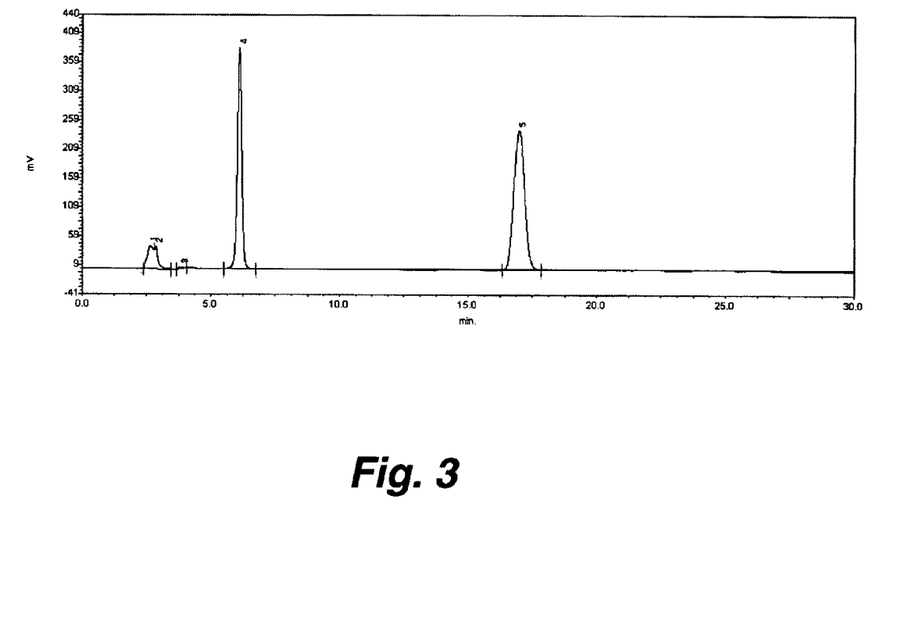
FIG. 3 shows a high performance liquid chromatographic (HPLC) profile of a resveratrol standard containing 100 ppm of trans-resveratrol and 100 ppm of piceid (i.e., resveratrol-O-glucoside). Trans-resveratrol was eluted at about 17 minutes; piceid was eluted at about 6 minutes.

The HPLC profile of the trans-resveratrol and piceid standards is shown in FIG. 3. The standards contained 100 ppm of trans-resveratrol and 100 ppm of piceid. Piceid was eluted at about 6 minutes from the pipe column. Trans-resveratrol was eluted at about 17 minutes from the pipe column.

Figure 4:
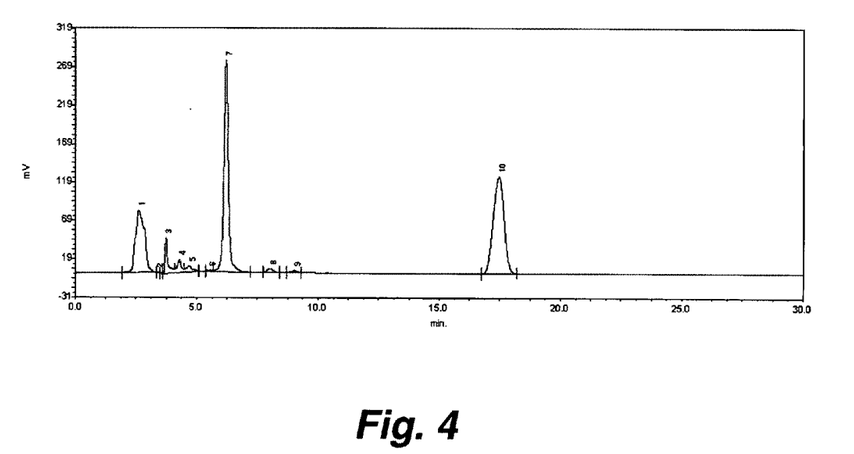

The HPLC profile of the resveratrol extracted from the in vitro resveratrol-rich callus tissue is shown in FIG. 4. The elution peaks of the resveratrol and piceid, respectively, were very similar to those of the standards, which had equal quantities of resveratrol and piceid (i.e., each containing 100 ppm) (FIG. 3), indicating that the proportion of the resveratrol and piceid in the in vitro resveratrol-rich callus tissue might be similar to that of the standards. The in vitro resveratrol-rich callus tissue was derived from the petiole of the cultivated plantlet of the wild-type *V. thunbergii*. The plantlet was developed from a shoot of the wild-type *V. thunbergii* after being cultivated in an MSO medium containing ½ MS medium and a carbohydrate for about 2 months. The in vitro resveratrol-rich callus tissue was maintained in a tissue culture system containing ½ MS medium, carbohydrate, 1.50 mg/L of NAA, and 0.5 mg/L of BA.

Figure 5:
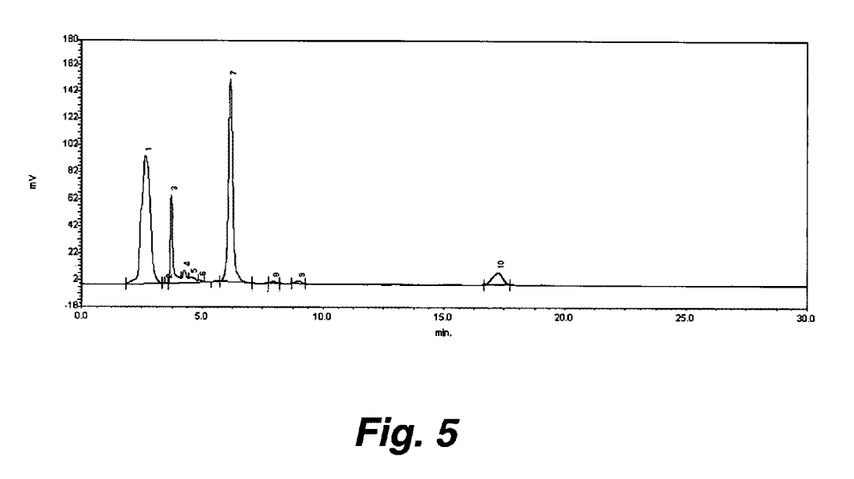
FIG. 5 shows a high performance liquid chromatographic (HPLC) profile of the various forms of resveratrol extracted from the callus tissue subcultured from the in vitro resveratrol-rich callus tissue for about 1 month. The subcultured callus tissue was cultivated in a subculture system containing a carbohydrate, a ½ MS medium, an about 1.86 mg/L of α-naphthaleneacetic acid (NAA) and an about 0.22 mg/L of 6-benzyl-aminopurine (BA). Piceid was the predominant resveratrol form of resveratrol in this subcultured callus tissue.

The HPLC profile of the resveratrol extracted from the subculture of the in vitro resveratrol-rich callus tissue is shown in FIG. 5. The elution profile of the subculture demonstrated a much smaller elution peak for resveratrol, as compared to the elution peak for piceid (FIG. 5). The subculture of the in vitro resveratrol-rich callus tissue was developed from inoculating a piece of the in vitro resveratrol-rich callus tissue to a subculture medium containing ½ MS medium containing 1.86 mg/L of NAA and 0.22 mg/L of BA, and maintaining the subculture for about 1 month.

Statistic Analysis

All experiments were carried out in triplicates. The statistical analysis was performed using Duncan's multiple range test (Ducan DB Biometrics, (1955), 11:1-42), 5% significance level.

Example 2

Differences in Calluses Produced by Different Explants

Figure 6:
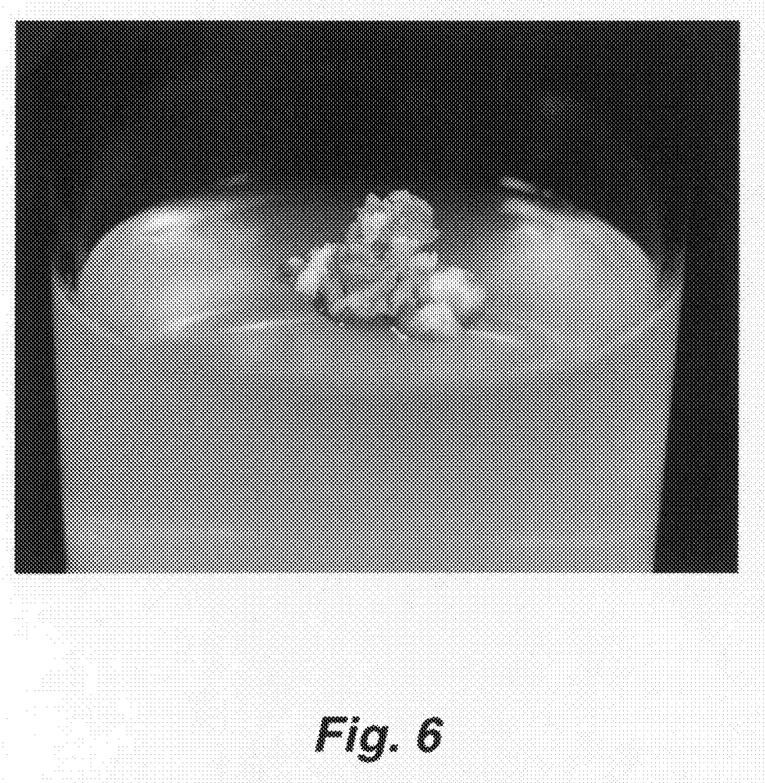
FIG. 6 shows callus formation from a leaf explant of wild-type *V. thunbergii*. The leaf explant was cultured in a tissue culture system containing a carbohydrate, a ½ MS medium, an about 1.5 mg/L of α-naphthaleneacetic acid (NAA) and an about 0.5 mg/L 6-benzyl-aminopurine (BA) for about 1 month. Only small calluses and roots were induced from the leaf explant.

The leaf, petiole (the base of leaf), and stem of in vitro cultured *Vitis thunbergii* Sieb. et Zucc. plant were tested as explants to induce calluses. The leaf tissue was not a good explant for induction of calluses. As shown in FIG. 6, after one month in the tissue culture system containing a ½ MS medium with 1.5 mg/L of NAA, and 0.5 mg/L of BA, most of the leaf explants only generated small calluses or roots.

Figure 7:
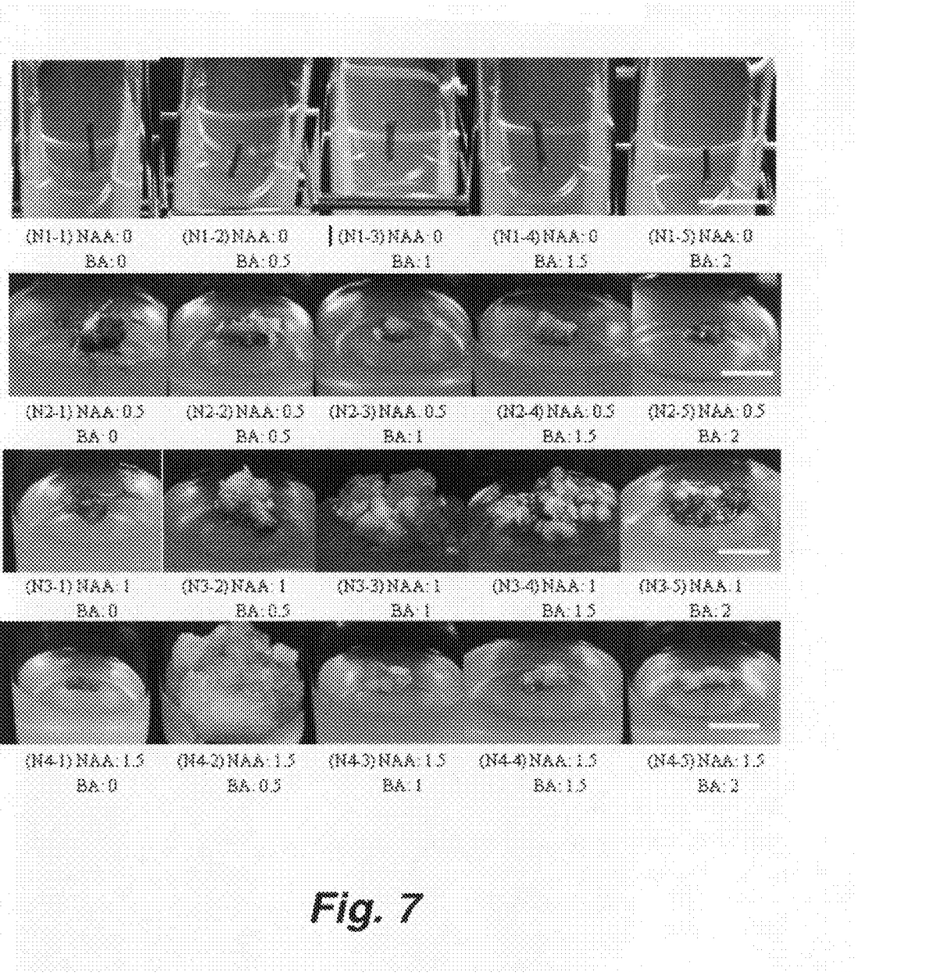
Figure 8:
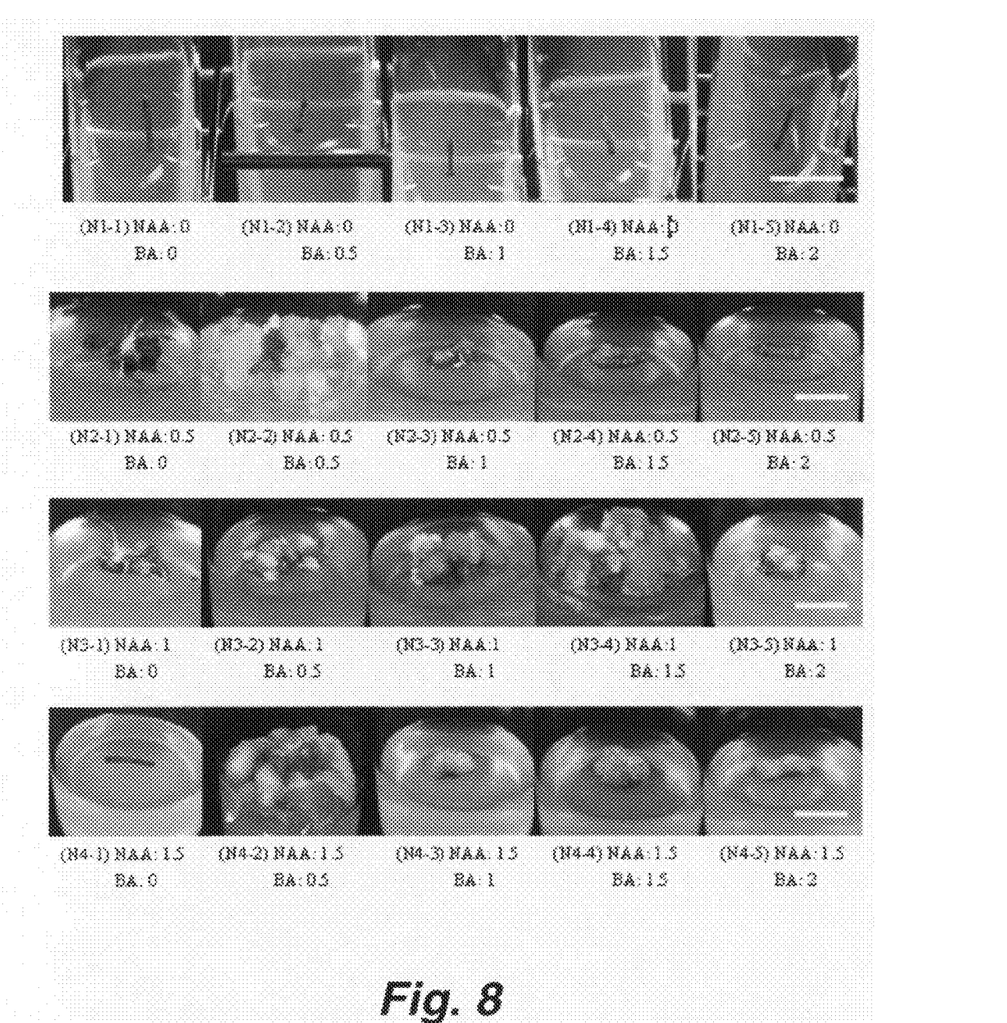

When stem (FIG. 7) or petiole (FIG. 8) explants were used, if the tissue culture media did not contain NAA, all explants became brown with no callus generation (FIGS. 7-8, N1-1~N1-5). If the tissue culture media contained NAA in the concentration range of 0.5-1 mg/L and no BA (FIGS. 7-8, N2-1, and N3-1), the petiole and stem segments developed roots instead of calluses. The callus tissue from the stem explant developed in the tissue culture system with the NAA at the concentration of 1.5 mg/L (FIGS. 7-8, N4-1) and no BA. No callus development was observed, however, when the petiole explant was cultivated at the NAA concentration of 1.5 mg/L with no BA. The induction of callus tissue, however, was not effective when NAA concentration was 2 mg/L. Most explants could only expand slightly without generating calluses.

As shown in FIGS. 7-8, stem tissues developed only roots in the N2-2 medium, but petiole tissues developed loose calluses in the same medium. The petiole tissues also developed loose calluses in N3-4 medium, while the stem tissues generated tumor shaped calluses in the same medium. It thus appears that different explant generated callus tissues of different size and shape in the same induction medium, with petiole explant clearly showing superior effect than the stem explant. In the N4-2 medium, however, both the petiole and stem produced loose calluses.

Example 3

Growth Rates and Resveratrol Contents in the In Vitro Resveratrol-Rich Callus Tissues and their Subcultures To study the resveratrol content in the callus subculture, well induced in vitro resveratrol-rich callus tissues from the stem or petiole explants of Example 2 were placed in a fresh culture containing the various solid subculture medium as indicated in Table 3 for about 1 month with the medium changed every two weeks to develop the subculture of the in vitro resveratrol-rich callus tissues. About 1 g of the fresh weight (FW) of the subcultured callus tissues was taken out from the subculture, and analyzed for the resveratrol content. As shown in Table 3, the media containing 1.5 mg/L NAA and 0.5 mg/L BA resulted in the highest resveratrol content in the subculture of the in vitro resveratrol-rich callus tissue from either the stem or the petiole explant. The control tissue was a callus tissue after being subcultured in an MS medium containing 1.86 mg/L of NAA and 0.22 mg/L of BA for at least 3 years.

TABLE 3

Influence of PGRs on Growth Rate and Total Resveratrol Content of the Subcultures of In Vitro Resveratrol-rich Callus Tissues Induced from Different Explants of *Vitis thunbergii* Sieb. et Zucc.

| PGR (mg/L) | | Original | Growth | Resveratrol content (mg/DW kg) | | |
|---|---|---|---|---|---|---|
| NAA | BA | Explant | rate | Piceid | Trans-Resveratrol | Total Content |
| 0.5 | 0.5 | petiole | 6.67b | 168.90 | 23.11 | 192.02 d* |
| 1 | 1 | stem | 6.49b | 2265.41 | 209.29 | 2474.71 c |
| 1.5 | 0.5 | petiole | 4.85b | 3616.36 | 77.65 | 3694.02 a |
| 1.5 | 0.5 | stem | 4.46b | 3208.37 | 88.80 | 3297.18 b |
| 1.86 | 0.22 | control[1] | 11.85a | 42.94 | 0.00 | 42.94 d |

Growth rate = (Final F.W. − Initial F.W.)/Initial F.W.
Values are means of 3 replicates ± S.E.
Means within a column followed by the same (a to d) letters are not significantly different by Duncan's multiple range test (P > 0.05).
[1]Control = subculture of the callus tissue in an MS medium containing 1.86 mg/L of NAA and 0.22 mg/L of BA for many generations.

The results of Table 3 demonstrated that the subculture medium containing 1.86 mg/L of NAA and 0.22 mg/L of BA provided the higher growth rate than other NAA and BA combination. However, the resveratrol content of the long term callus tissues (i.e., the control) was substantially lower than other subcultures having various PGRs combinations of NAA and BA. Among the various PGRs combinations, the subculture medium containing 1.5 mg/L of NAA and 0.5 mg/L of BA produced the callus tissue containing the highest amount of resveratrol. Also, in the callus subculture, the predominant form of resveratrol is piceid (i.e., resveratrol-O-glucoside).

The resveratrol contents in the in vitro resveratrol-rich callus tissue derived from the petiole explant of the *V. thunbergii*, and its three subsequent subcultures were analyzed. The subsequent subcultures were conducted in a ½ MS medium containing 1.86 mg/L of NAA and 0.22 mg/L of BA.

Each of the tissue samples was cultivated in the designated tissue culture or subculture medium for about 1 month. The results were shown in Table 4.

TABLE 4

Resveratrol Contents in Various Subcultures of the In Vitro Resveratrol-Rich Callus Tissues of *Vitis thunbergii* Sieb. et Zucc.

| No. of Subculture | Subculture Medium | Resveratrol Content (mg/Kg DW) | | |
|---|---|---|---|---|
| | | Trans-Resveratrol | Piceid | Total |
| In vitro Resveratrol-rich Callus tissue (No Subculture) | ½ MS + Carbohydrate + 1.5 mg/L NAA + 0.5 mg/L BA | 3215.79 ± 84.78 | 4855.47 ± 164.20 | 8071.26 ± 232.77 |
| 1st Subculture | ½ MS + Carbohydrate + 1.86 mg/L NAA + 0.22 mg/L BA | 111.56 ± 111.72 | 3020.02 ± 502.18 | 3131.58 ± 404.67 |
| 2nd Subculture | ½ MS + Carbohydrate + 1.86 mg/L NAA + 0.22 mg/L BA | 11.53 ± 1.28 | 934.72 ± 168.10 | 946.25 ± 168.70 |
| 3rd Subculture | ½ MS + Carbohydrate + 1.86 mg/L NAA + 0.22 mg/L BA | 8.37 ± 1.59 | 520.54 ± 82.11 | 528.91 ± 82.39 |
| Dried Leaves and twigs of Wild-Type *V. thunbergii* | N.A. | 20.88 ± 1.06 | 42.75 ± 1.78 | 63.63 ± 2.82 |

Values are means of 3 replicates ± S.E.

As shown in FIG. 4 and Table 4, the in vitro resveratrol-rich callus tissue contained about 8,000 mg/kg DW of total resveratrol, of which about 3,200 mg/kg DW were trans-resveratrol and 4,800 mg/kg DW were piceid. Also, as shown in Table 4, the resveratrol content decreased after each passage of the subculture of the in vitro resveratrol-rich callus tissue, with the resveratrol amount reduced to about 10 mg/kg DW after 3 passages. The total resveratrol amount in the 1st, 2nd, and 3rd subcultures were about 3,000 mg/kg DW, 1,000 mg/kg DW, and 500 mg/kg DW, as compared to the in vitro resveratrol-rich callus tissue, which had about 8,000 mg/kg DW of total resveratrol, and the dried leaves and twigs of the commercially available wild-type *V. thunbergii*, which had a total resveratrol of about 65 mg/kg DW. The results demonstrated that the in vitro resveratrol-rich callus tissue and at least its first three subcultures contained far greater total resveratrol than the naturally occurred dried leaves of *V. thunbergii* and therefore could be used as a valuable source of naturally produced resveratrol. Also, as shown in FIG. 5 and Table 4, because more than half of the resveratrol in the in vitro resveratrol-rich callus tissue and the majority of the resveratrol in the subcultures were in the piceid form, i.e., resveratrol-O-glucoside form, these in vitro tissues were particularly a great source for naturally produced piceid.

The embodiments illustrated and discussed in this specification are intended only to teach those skilled in the art the best way known to the inventors to make and use the invention. Nothing in this specification should be considered as limiting the scope of the present invention. The above-described embodiments of the invention may be modified or varied, and elements added or omitted, without departing from the invention, as appreciated by those skilled in the art in light of the above teachings. It is therefore to be understood that, within the scope of the claims and their equivalents, the invention may be practiced otherwise than as specifically described.

What is claimed is:

1. An in vitro resveratrol-rich callus tissue derived from *Vitis thunbergii* Sieb. et Zucc. (*V. thunbergii*),
   wherein said in vitro resveratrol-rich callus tissue is a callus tissue induced in a tissue culture system containing one or more plant growth regulators (PGRs) and cultured from a stem or a petiole tissue explant of a wild type of *V. thunbergii* or a cultivated plantlet of *V. thunbergii*; and
   wherein said in vitro resveratrol-rich callus tissue contains said resveratrol in the amount of about 1,000 to 10,000 mg/kg of dried weight.

2. The in vitro resveratrol-rich callus tissue according to claim 1, wherein said in vitro resveratrol-rich callus tissue contains said resveratrol in the amount of about 3,000 to 8,000 mg/kg of dried weight.

3. The *in vitro* resveratrol-rich callus tissue according to claim 1, wherein said in vitro resveratrol-rich callus tissue is cultured from said petiole tissue explant of said wild type of *V. thunbergii* or cultivated plantlet of *V. thunbergii*.

4. The *in vitro* resveratrol-rich callus tissue according to claim 1, wherein said cultivated plantlet is grown from a shoot of said wild type of *V. thunbergii* in a plantlet culture system comprising a carbohydrate and a Murashige and Skoog basic salt medium (MS medium) without any plant growth regulator,
   wherein said MS medium comprises sodium, potassium, nitrate, ammonium, magnesium, sulfate, calcium, iron, chloride, phosphate, manganese, iodine, borate, zinc, copper, molybdenum, and cobalt, and
   wherein said carbohydrate in said plantlet culture system is at least one selected from the group consisting of myo-inositol or sucrose.

5. The in vitro resveratrol-rich callus tissue according to claim 4, wherein said stem or petiole tissue explant is suitable for culturing said in vitro resveratrol-rich callus tissue after being cultivated in said plantlet culture system for about 2 months.

6. The in vitro resveratrol-rich callus tissue according to claim 1, wherein said tissue culture system further comprises a salt medium which is a Murashige and Skoog basic salt medium (MS medium) comprising sodium, potassium, nitrate, ammonium, magnesium, sulfate, calcium, iron, chloride, phosphate, manganese, iodine, borate, zinc, copper, molybdenum, and cobalt.

7. The in vitro resveratrol-rich callus tissue according to claim 1, wherein said one or more PGRs are α-naphthaleneacetic acid (NAA) and/or 6-benzyl-aminopurine (BA).

8. The in vitro resveratrol-rich callus tissue according to claim 7, wherein said one or more PGRs are said NAA at about 1.5 mg/L and said BA at about 0.5 mg/L.

9. The in vitro resveratrol-rich callus tissue according to claim 1, wherein said tissue culture system further comprises a carbohydrate selected from the group consisting of myo-inositol, sucrose, and a mixture thereof.

10. The in vitro resveratrol-rich callus tissue according to claim 1, wherein said tissue culture system further comprises a vitamin selected from the group consisting of thiamine HCl, pyridoxine HCl, nicotinic acid, and mixtures thereof.

11. The in vitro resveratrol-rich callus tissue according to claim 1, wherein said tissue culture system has a pH of about 5 to 7.

12. The in vitro resveratrol-rich callus tissue according to claim 1, wherein said resveratrol in said in vitro resveratrol-rich callus tissue comprises resveratrol and resveratrol-O-glucoside.

13. The in vitro resveratrol-rich callus tissue according to claim 1, wherein said in vitro resveratrol-rich callus tissue is suitable for harvest or forming a subculture after growing in said tissue culture system for about 30 days.

14. The in vitro resveratrol-rich callus tissue according to claim 1, wherein said tissue culture system comprises a tissue culture medium which contains a carbohydrate, ½Murashige and Skoog basic salt medium (MS medium), about 1.5 mg/L of α-naphthaleneacetic acid (NAA) and about 0.5 mg/L 6-benzyl-aminopurine (BA).

15. The in vitro resveratrol-rich callus tissue according to claim 13, wherein said subculture of said in vitro resveratrol-rich callus tissue comprises a reduced amount of said resveratrol than said in vitro resveratrol-rich callus tissue.

16. The in vitro resveratrol-rich callus tissue according to claim 15, wherein said subculture of said in vitro resveratrol-rich callus tissue comprises said resveratrol in the amount of 500 to 4000 mg/kg of dried weight.

17. The in vitro resveratrol-rich callus tissue according to claim 1, wherein said tissue culture system is a solid culture system.

* * * * *